United States Patent
Ryu et al.

(10) Patent No.: US 8,277,848 B2
(45) Date of Patent: Oct. 2, 2012

(54) METHOD FOR PREPARING AQUEOUS SOLUTION OF HIGH-CONCENTRATION CALCIUM PHOSPHATE STABLE IN NEUTRAL PH RANGE

(75) Inventors: Hyun Seung Ryu, Yongin-si (KR); Mi Young Ryu, Seongnam-si (KR); Jun Hyuk Seo, Seoul (KR); Gyu Dong Jang, Seoul (KR); Baek Il Kim, Seoul (KR)

(73) Assignee: Bioalpha Inc. (KR)

( * ) Notice: Subject to any disclaimer, the term of this patent is extended or adjusted under 35 U.S.C. 154(b) by 0 days.

(21) Appl. No.: 13/185,634

(22) Filed: Jul. 19, 2011

(65) Prior Publication Data

US 2012/0183625 A1    Jul. 19, 2012

(30) Foreign Application Priority Data

Jan. 18, 2011   (KR) .................. 10-2011-0004956

(51) Int. Cl.
*A61K 33/42*    (2006.01)

(52) U.S. Cl. ..................................... 424/602
(58) Field of Classification Search .................. None
See application file for complete search history.

(56) References Cited

U.S. PATENT DOCUMENTS 4,183,915 A * 1/1980 Gaffar et al. .................. 424/52

* cited by examiner

*Primary Examiner* — Noble Jarrell
*Assistant Examiner* — Mark V Stevens
(74) *Attorney, Agent, or Firm* — Cantor Colburn LLP

(57) ABSTRACT

Disclosed herein is a method for preparing an aqueous solution of high-concentration calcium phosphate, the method comprising the steps of: preparing an acidic aqueous solution using an acidic chelating agent; and dissolving a calcium phosphate-based compound in the acidic aqueous solution, and then adding a pH-adjusting agent to the acidic aqueous solution to adjust the pH of the acidic aqueous solution. The disclosed aqueous solution does not form a precipitate after neutralization so that it can be used in various calcium-containing products, including foods, drugs, or quasi-drugs.

11 Claims, 4 Drawing Sheets

Fig. 4

| | SEM photograph | Magnification |
|---|---|---|
| Comparative Example: Aqueous solution of 0.1% citric acid containing NaOH (final pH: 6) | | X10,000 |
| Example: Aqueous solution of 0.1% citric acid containing 0.0024 wt% phosphoric acid, 0.1 wt% n-CAP, and NaOH (final pH: 6) | | X10,000 |

# METHOD FOR PREPARING AQUEOUS SOLUTION OF HIGH-CONCENTRATION CALCIUM PHOSPHATE STABLE IN NEUTRAL PH RANGE

TECHNICAL FIELD

The present invention relates to a method for preparing an aqueous calcium phosphate solution, and more particularly to a method for preparing an aqueous solution of high-concentration calcium phosphate, in which the aqueous solution is stable in the neutral pH range and does not form a precipitate after neutralization so that it can be used in various calcium-containing products, including foods, drugs, or quasi-drugs.

BACKGROUND ART

It is known that calcium, the most common mineral in the human body, is found as a calcium phosphate salt mainly in bones and teeth, and thus is important to maintain bone strength. Particularly, a trace amount of calcium present in blood and cells has important metabolic effects, such as regulation of cardiac rhythm, activation of muscles and nerves, blood coagulation, and increases in enzymatic activity and cell membrane permeability.

Because more than 99% of the human body's calcium reserves are stored in bones and teeth, calcium is important for bone growth and formation and during the lactation period. Specifically, for infants, adolescents, and pregnant and nursing women, calcium intake is very important, and foods and various supplements are used to meet the recommended daily calcium intake. Thus, calcium-containing products, including calcium-containing foods, drugs and quasi-drugs, have been actively developed.

The absorption of calcium is greatly influenced by dietary components and in vivo factors. Dietary components that can be externally controlled include vitamin D, lactose, protein, amino acid, lipid, phosphoric acid, the calcium-to-phosphorus ratio, oxalic acid, and the like. Among them, protein, lipid, phosphoric acid and oxalic acid interfere with the absorption of calcium when they are taken in excessive amounts, whereas vitamin D, lactose and amino acid help the absorption of calcium. Particularly, it is known that the absorption rate of calcium is good when the molar ratio of calcium and phosphorus is 1:1 to 2:1, because this ratio is similar to the calcium-to-phosphorus ratio of a calcium phosphate-based compound forming the bone of the human body.

When supplements other than foods are used to take calcium, the intake of calcium can vary depending on the formulation of the supplements, rather than depending on dietary components. Calcium supplements that are in common use are prepared in the form of tablets which take 4-6 hours to dissolve in the body. When calcium supplements are prepared as capsules, the supplements dissolve more easily than calcium supplement tablets and are more easily absorbed into the body. In other words, because the rate of absorption of calcium into the body has a great significance, whether calcium was prepared in a form which can be easily absorbed into the body after intake can be considered as an important factor.

Meanwhile, it is well known that tooth hypersensitivity occurring die to damaged teeth can be relieved by remineralization using a calcium phosphate compound. Specifically, tooth hypersensitivity is relieved by treating dentinal tubules, exposed due to the decalcification of teeth enamel, with hydroxyapatite, and this relief can be achieved by precipitation of an aqueous solution containing a high concentration of calcium phosphate.

With respect to the requirements of an aqueous calcium phosphate solution for tooth remineralization, the aqueous solution should form a precipitate on the tooth surface when applied to the tooth, and the stability of pH and ions of the solution should be well maintained during storage.

DISCLOSURE

Technical Problem

Accordingly, it is an object of the present invention to provide a method for preparing an aqueous solution of high-concentration calcium phosphate, in which the aqueous solution is stable in the neutral pH range and does not form a precipitate after neutralization so that it can be used in various calcium-containing products, foods, drugs, or quasi-drugs.

Technical Solution

To achieve the above object, the present invention provides a method for preparing an aqueous solution of high-concentration calcium phosphate, the method comprising the steps of: preparing an acidic aqueous solution using an acidic chelating agent; and dissolving a calcium phosphate-based compound in the acidic aqueous solution, and then adding a pH-adjusting agent to the acidic solution to adjust the pH of the acidic aqueous solution.

According to the present invention, phosphoric acid ($H_3PO_4$) may further be added to the acidic aqueous solution.

The acidic chelating agent is preferably any one selected from among citric acid and EDTA (ethylene diamine tetra-acetic acid).

The calcium phosphate-based compound is preferably at least one selected from among hydroxyapatite (HA; $Ca_{10}(PO_4)_6(OH)_2$), carbonated apatite (CAP; $Ca_{10}(PO_4)_6 \cdot (X(OH)_{2=3})$), tricalcium phosphate (TCP; $Ca_3(PO_4)_2$), and calcium hydrogen phosphate ($CaHPO_4 \cdot nH_2O$).

The pH-adjusting agent is at least one selected from among sodium hydroxide and sodium hydrogen carbonate.

The acidic aqueous solution and the calcium phosphate-based compound are preferably an aqueous citric acid solution and nano-sized carbonated apatite (n-CAP), respectively.

The citric acid and the n-CAP are preferably used at concentrations of 0.3 wt % or less and 0.25 wt % or less, respectively, based on the total weight of the aqueous solution.

The citric acid and the n-CAP are preferably used at concentrations of 0.1 wt %, respectively, based on the total weight of the aqueous solution.

The pH of the aqueous solution is preferably in the range of 5.5 to 6.1.

The phosphoric acid is preferably added in an amount of 0.0012~0.006 wt % based on the total weight of the aqueous solution.

The phosphoric acid is preferably added in an amount of 0.0024 wt % based on the total weight of the aqueous solution.

Advantageous Effects

According to the present invention, there is provided an aqueous solution of high-concentration calcium phosphate, which does not form a precipitate after neutralization, and thus is stable in the neutral pH range.

The aqueous solution of the present invention has an optimal calcium-to-phosphorus ratio suitable for the in vivo absorption of calcium while it is stable in the neutral pH range. Accordingly, the aqueous solution of the present invention can be used in juices, ionic beverages and carbonated beverages, which has a pH lower than neutral pH, and thus it can promote the intake and absorption of calcium and prevent tooth erosion.

BRIEF DESCRIPTION OF DRAWINGS

FIG. 4 shows surface SEM photographs of hydroxyapatite treated with an aqueous citric acid solution containing or not containing n-CAP.

MODE FOR INVENTION

An aqueous solution of high-concentration calcium phosphate which is prepared according to the present invention can be used for the intake of calcium and treatment of damaged teeth.

The aqueous calcium phosphate solution can be prepared using a compound based on calcium and phosphorus. Examples of the calcium phosphate-based compound that can be dissolved in an acidic solution include hydroxyapatite (HA; $Ca_{10}(PO_4)_6(OH)_2$), carbonated apatite (CAP; $Ca_{10}(PO_4)_6.(X(OH)_2YCO_3)$), tricalcium phosphate (TCP, $Ca_3(PO_4)_2$), and calcium hydrogen phosphate ($CaHPO_4.nH_2O$).

The calcium-to-phosphorus ratio of the calcium phosphate-based compounds is in the range from 1:1 to 2:1 in which the absorption of calcium into the human body can be promoted. Specifically, the aqueous solution of high-concentration calcium phosphate can be prepared using a calcium phosphate-based compound having a calcium-to-phosphate ratio ranging from 1:1 to 2:1 can be used.

Figure 1:
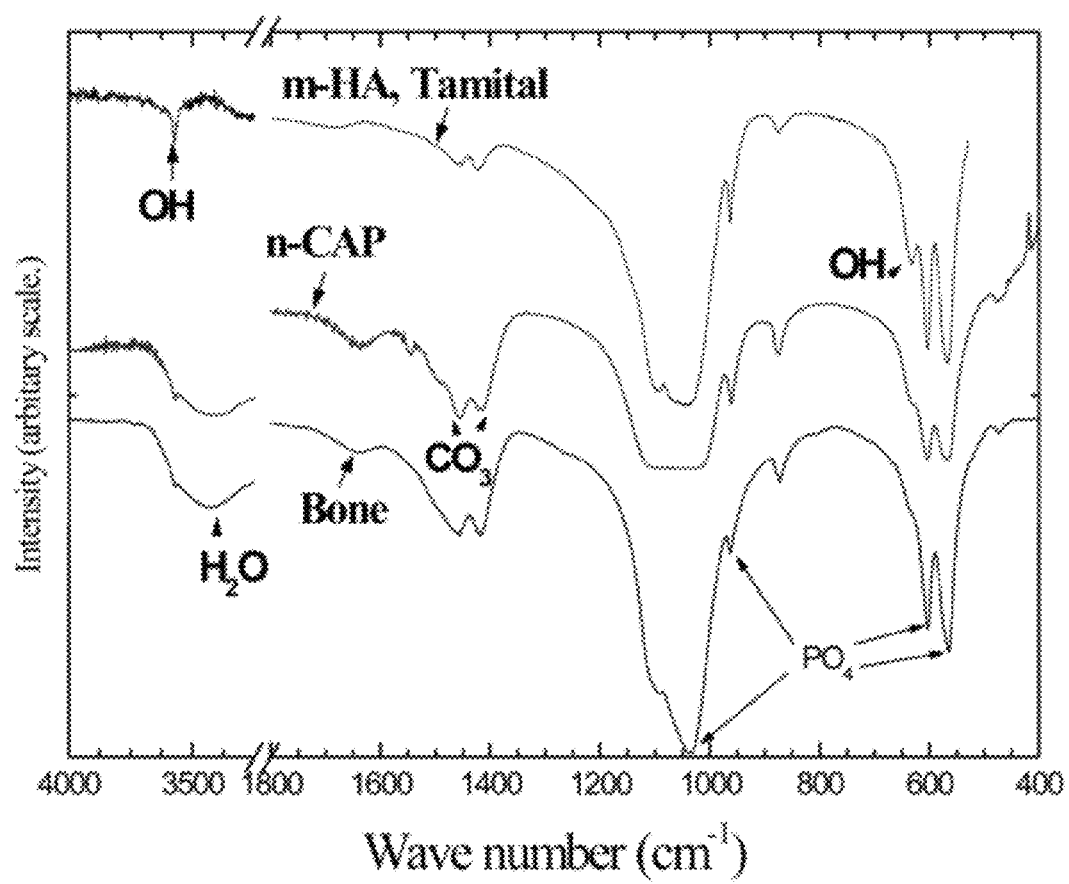
FIG. 1 shows the FT-IR spectra of hydroxyapatite, n-CAP, and bone.

More than 99% of the human body's calcium reserves are stored in bones and teeth, and for this reason, a preparation having a calcium-to-phosphate molar ratio of 1.66:1 similar to that of the human body skeletal has a very high rate of absorption into the human body. Considering this fact, in order to increase the absorption of calcium, carbonated apatite having a Ca:P ratio of 1.66:1 and containing a carboxyl group is preferably used as a calcium source, and in order to increase the dissolution rate of calcium in a solution, nano-sized carbonated apatite (n-CAP) is preferably used.

n-CAP is a hydroxyapatite ($Ca_{10}(PO_4)_6(OH)_2$) substituted with a very small amount of a carboxyl group and is identical to the mineral component of bone. In order to compare n-CAP and general hydroxyapatite with bone, FT-IR (Fourier Transform Infra-red spectrometer) analysis was carried out. As a result, as can be seen in FIG. 1, n-CAP showed the same analysis results as those for the bone.

The method for preparation of the aqueous calcium phosphate solution according to the present invention consists mainly of: a step of dissolving a calcium phosphate-based solution; and a step of adjusting the pH of the solution. To dissolve the calcium phosphate-based compound, an acidic chelating agent can be used.

In the present invention, citric acid ($C_6H_8O_7$) or ethylene diamine tetra-acetic acid (EDTA; $C_{10}H_{16}N_2O_8$), for example, can be used as an organic acid callable of forming chelates with calcium ions after dissolution of calcium phosphate. In addition, various acidic chelating agents may be used in the present invention.

Calcium phosphate-based compounds dissolve in an acidic solution, particularly in a solution having a pH of 2 or less. However, if the pH of the solution is increased to a value greater than 3, the calcium phosphate-based compounds precipitate in the order of their increasing solubility in the acidic pH range. Particularly, dicalcium phosphate dehydrate (DCPD; $CaHPO_4.2H_2O$) which is stable at a pH of 4.2 or less first precipitates.

Figure 2:
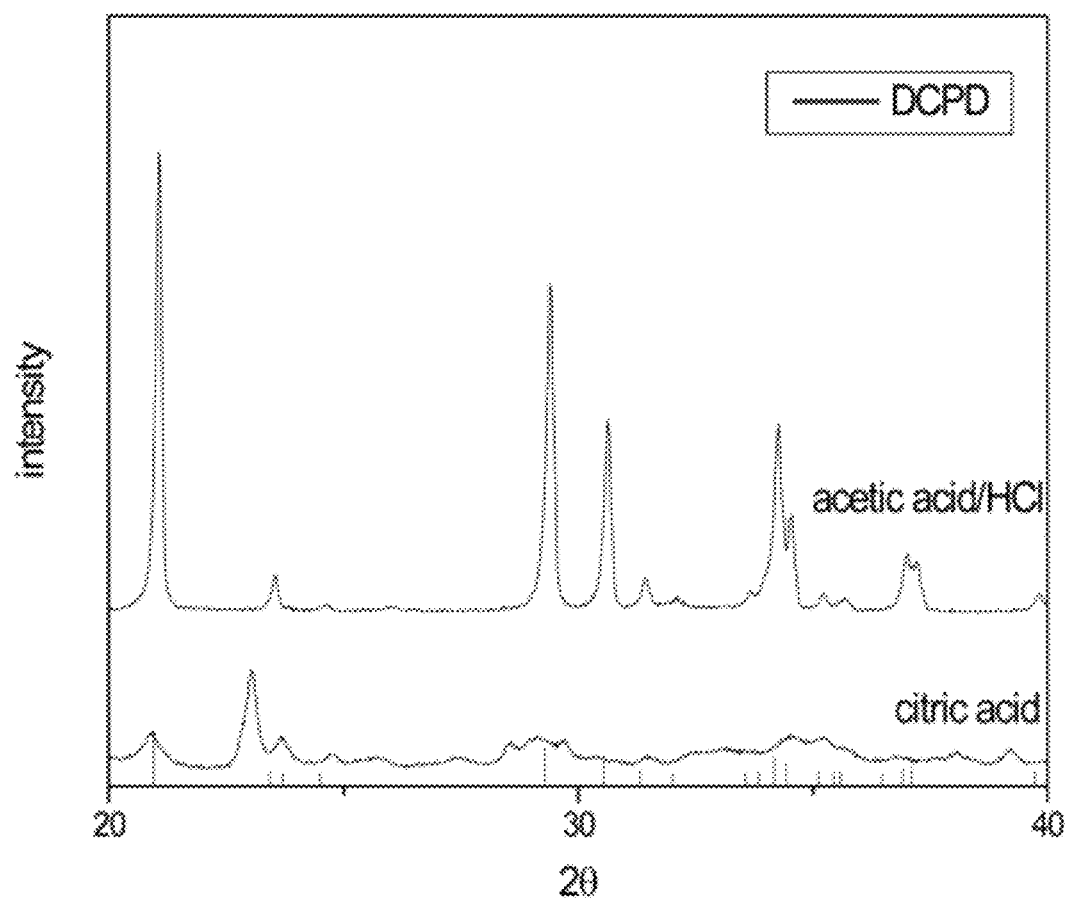
FIG. 2 shows the X-ray diffraction patterns of organic materials that precipitated during a pH adjustment process after n-CAP had been dissolved in various acidic solutions.

When n-CAP is dissolved using an organic or inorganic acid incapable of forming chelates and then the pH of the solution is increased, a precipitate is rapidly formed. In order to confirm this fact, the present inventors carried out experiments using citric acid and acetic acid, and the formed precipitates were separated from the solution and analyzed by XRD. The results of the analysis are shown in FIG. 2. As can be seen in FIG. 2, a single-phase DCPD was produced.

From such results, it can be seen that a chelate solution having a pH of 3 or less is suitable for preparation of an aqueous calcium phosphate solution stable at neutral pH and that citric acid or EDTA, a food or drug additive, is preferably used in order to apply the aqueous solution to foods, drugs or quasi-drugs.

Figure 3:
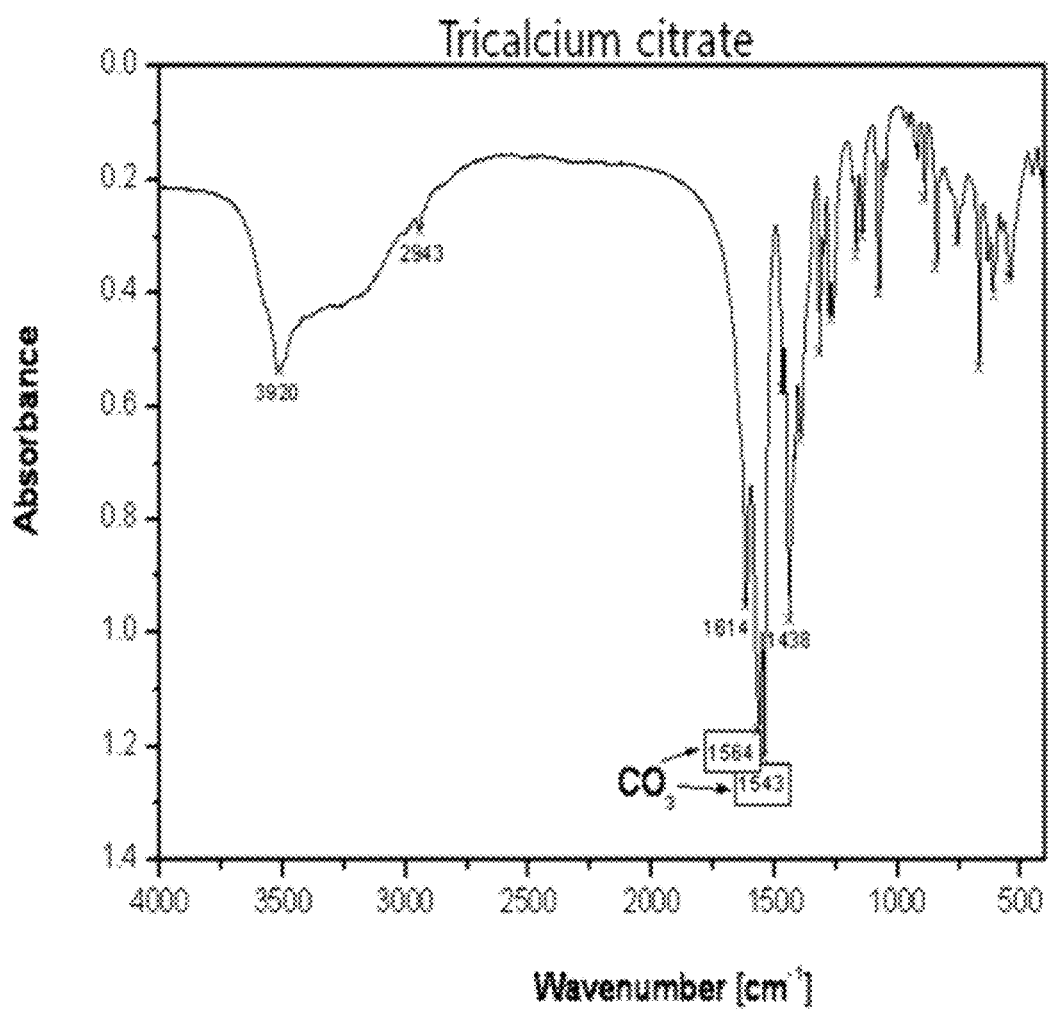
FIG. 3 shows the FT-IR spectrum of a precipitate formed in a high-concentration citric acid solution and the chemical structure of a substance corresponding to the precipitate.
Figure 3:
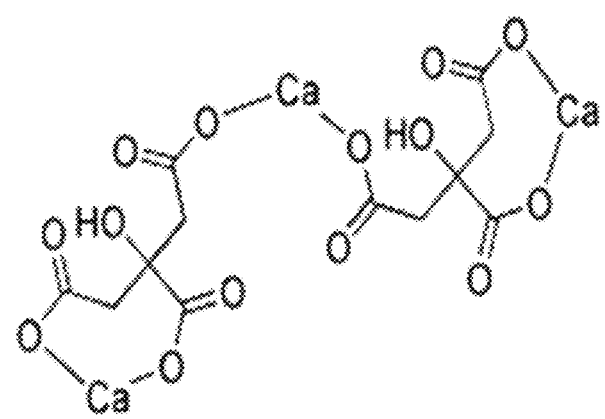

When an acidic chelate solution is made using citric acid as a chelating agent, after which n-CAP, a calcium phosphate compound, is dissolved in the acidic chelate solution, tricalcium citrate can be formed by calcium, a decomposition product of n-CAP, with citric acid. Specifically, when a citric acid solution having a citric acid concentration of more than 0.3%, after which n-CAP is added to the solution until it reaches the solubility limit, an organic precipitate is rapidly formed after 1 day. When the precipitate is separated from the solution and analyzed by FT-IR, it can be seen in FIG. 3 that tricalcium citrate was produced.

Because the solubility of tricalcium citrate, the reaction product of calcium ions and citric acid, is as low as 0.1 g/100 ml, the tricalcium citrate is rapidly bonded when it reaches an oversaturated state, thereby forming a precipitate. For this reason, for the preparation of the aqueous solution of high-concentration calcium phosphate, the solubility of tricalcium citrate should be considered. For this purpose, in the present invention, citric acid is used at a concentration of 0.3 wt % or less, and preferably 0.1%, based on the total weight of the aqueous calcium phosphate solution.

Table 1 below shows the contents of calcium and phosphate, which can be stably present without forming tricalcium citrate in solutions when the concentration of citric acid is increased in order to increase the dissolution of citric acid. Table 1 shows the concentrations of calcium and phosphorus in solutions which were stored at room temperature for one week without adjusting the pH of the solutions.

As can be seen in Table 1, as the concentration of citric acid increases, the dissolution of n-CAP increases, but the formation of the precipitate increases, the stability of the solutions is not ensured even in the acidic state, and the amount of the precipitate increases with the passage of time.

Although the molecular weight of n-CAP cannot be presented, the contents of calcium and phosphorus in n-CAP were calculated considering the molecular weight of HA (1004 g/mole), because the contents of calcium and phosphorus in n-CAP are identical to those of HA. As a result, the concentrations of citric acid and n-CAP in solutions of low-concentration citric acid were similar to each other; however, as the concentration of citric acid was increased, n-CAP corresponding to 50% or less of the citric acid concentration was dissolved.

TABLE 1

Contents of calcium and phosphorus as a function of citric acid concentration

| Citric acid concentration | 0.10% | 0.30% | 0.50% | 0.70% | 1% |
|---|---|---|---|---|---|
| Calcium | 0.043% | 0.099% | 0.120% | 0.155% | 0.200% |
| Phosphorus | 0.022% | 0.066% | 0.105% | 0.141% | 0.196% |
| Calcium: phosphorus | 1.5:1 | 1.2:1 | 0.89:1 | 0.85:1 | 0.79:1 |
| n-CAP content | 0.10% | 0.25% | 0.30% | 0.39% | 0.50% |

(%: wt %)

As shown in Table 1 above, when the concentrations of calcium and phosphorus as a function of citric acid concentration are compared with each other, the calcium-to-phosphorus ratio is 1.5:1 at a citric acid concentration of 0.1%, and as the citric acid concentration increased, the relative amount of calcium decreases, and the calcium-to-phosphorus ratio reaches about 0.8:1 at a citric acid concentration of 1%. Because excessive amounts of calcium and citric acid precipitate to form tricalcium citrate, the amount of calcium decreases, and for this reason, the intake of calcium deviates from the active range.

Thus, from the point of view of increasing the absorption rate of calcium, the concentrations of citric acid and n-CAP are preferably 0.3% or less and 0.25%, respectively, so that the calcium-to-phosphorus ratio is in the range from 1:1 to 2:1. Particularly, when the concentrations of citric acid and n-CAP are 0.1%, respectively, the calcium-to-phosphorus ratio is 1.5:1 close to a ratio of 1.66:1 at which the rate of absorption of calcium into the body is the highest, so that an optimal solution suitable for absorption of calcium can be prepared.

When citric acid is used as the acidic substance, a stable calcium solution having a pH of 6 can be prepared regardless of the kind of pH-adjusting agent.

Based on the results shown in Table 1, a pH-adjusting process was carried out using a sample of a 0.1% citric acid-containing solution in which the calcium-to-phosphorus ratio is most similar to that of bone. As the pH-adjusting agent, a basic substance such as sodium hydroxide (NaOH) or sodium hydrogen carbonate ($NaHCO_3$) was used, and both sodium hydroxide (NaOH) and sodium hydrogen carbonate ($NaHCO_3$) did not form a precipitate even when the pH of the solution was increased.

The pH of the aqueous calcium phosphate solution of the present invention is preferably in the range from 5.5 to 6.1. The hydroxyapatite of teeth dissolves at acidic pH, and the solubility thereof varies according to its stoichiometry. When the Ca/P ratio of the calcium phosphate-based compound is 1.66:1, the compound shows a stable behavior at a pH of 4.2 or more, but if the ratio is lowered to 1.5:1, the compound will dissolve at a pH of less than 5.5. In other words, in order to provide a stable aqueous solution which does not cause tooth erosion, the final pH of the aqueous solution should be maintained at 5.5 or more. Meanwhile, when the pH of the solution is more than 6.1, the pH will be rapidly increased due to an excessive amount of the basic substance such that it will be difficult to control, and the dissolution stability of n-CAP will be reduced so that the stability of the product cannot be ensured.

In an embodiment of the present invention, in an aqueous solution of 0.1 g of n-CAP in 100 ml of a 0.1% citric acid-containing solution, 15 μg of sodium hydroxide or 0.05 g of sodium hydrogen carbonate was required to adjust the final pH of the solution to 6. This composition allowed the preparation of an aqueous solution of high-concentration calcium which is stable in the neutral pH range.

A calcium phosphate solution for tooth remineralization should be a stable solution which does not form a precipitate even in the neutral pH range, and when it is applied to teeth, it should rapidly forms a precipitate. For rapid precipitation of minerals, an aqueous calcium phosphate solution should have optimal conditions in which it can form a precipitate while maintaining an oversaturated state.

In the present invention, in order to promote the precipitation of hydroxyapatite for rapid tooth remineralization, the content of phosphorus in the calcium phosphate solution was increased. For additional supply of phosphorus, phosphoric acid ($H_3PO_4$), for example, may be added to the aqueous calcium phosphate solution. Because the kind and ratio of phosphoric acid ions in a solution vary depending on the concentration thereof, the region in which $H_3PO_4$ and $H_2PO_4$ are present in the same amount should be selected so that the stability of n-CAP is maintained while the precipitation thereof is not interfered with.

For this purpose, in the present invention, the concentration of phosphoric acid is preferably in the range from 0.0012% to 0.006% (from 0.01 to 0.05 mol/l). If phosphoric acid is added at a concentration higher than the upper limit of this range, there will be a problem in that the calcium-to-phosphorus ratio decreases to 1:1 or less, and thus the absorption and precipitation of calcium are difficult.

In a specific embodiment of the present invention, a 85% phosphoric acid ($H_3PO_4$)-containing aqueous solution was added to a 0.1% citric acid-containing aqueous solution in an amount of 0.0024 wt % (0.02 mol/l) based on the total weight of the aqueous solution to prepare an acidic aqueous solution, after which n-CAP was dissolved therein at a concentration of 0.1%, and the pH of the solution was carried out. An experiment carried out by the present invention revealed that the prepared aqueous solution of high-concentration calcium phosphate rapidly forms a precipitate on HA pellets compared to a solution containing no phosphoric acid.

Meanwhile, FIG. 4 shows surface SEM photographs of HA pellets (having the same components as those of tooth enamel) treated with an aqueous citric acid solution containing or not containing n-CAP.

In order to examine the effect of n-CAP, a mixed solution of 0.1% citric acid and NaOH was used as a control and was adjusted to a final pH of 6. To examine remineralization properties, a solution containing 0.1 wt % citric acid, 0.0024 wt % phosphoric acid, 0.1 wt % n-CAP and NaOH and adjusted to a final pH of 6 was used. HA pellets were immersed in each of the solutions for 1 day, after which the surface of the HA pellets was analyzed by SEM at 10,000× magnification.

As can be seen in FIG. 4, when no n-CAP was added, a large amount of HA was dissolved so that holes having a size of about 1 μm were formed on the HA pellet surface, even though the final pH of the solution was adjusted to a neutral pH of 6. On the other hand, in the case of the aqueous solution of high-concentration calcium phosphate containing n-CAP according to the present invention, the HA surface was not dissolved and fine particles having a size of a few nanometers were aggregated on the surface.

From such results, it can be seen that the aqueous solution of high-concentration calcium phosphate prevents tooth erosion and also promotes the remineralization of tooth enamel and is advantageous for the occlusion of dentinal tubules.

INDUSTRIAL APPLICABILITY

As described above, the aqueous solution of high-concentration calcium phosphate according to the present invention does not form a precipitate after neutralization, and thus can be used in various calcium-containing products, foods, drugs, or quasi-drugs.

More specifically, the aqueous solution of calcium phosphate according to the present invention can be used in various beverages to increase the intake and absorption of calcium and to prevent tooth erosion. The aqueous calcium phosphate solution of the present invention has a calcium-to-phosphorus ratio optimal for the in vivo absorption of calcium and is stable in the neutral pH range, and thus can be used in juices, ionic beverages and carbonated beverages, which have a pH lower than neutral pH.

Calcium taken through the aqueous solution of the present invention is stored in bones and teeth, and a calcium beverage having a high calcium absorption rate can be prepared using the inventive aqueous solution having a Ca:P ratio of 1.66:1. Particularly, because the absorption rate of calcium is increased by protein, the aqueous solution of the present invention can be used in various milk products so as to maximize the effect thereof.

It is known that commercially available ionic beverages and carbonated beverages cause tooth erosion due to their low pH. Intake of an ionic beverage or carbonated beverage containing the aqueous solution of high-concentration calcium phosphate according to the present invention can prevent tooth erosion. However, because the calcium phosphate compound in the aqueous solution of the present invention can form a precipitate at high temperature, the aqueous solution of the present invention can be used in products which are stored at room temperature or under cold conditions.

The aqueous solution of the present invention can be used in calcium precipitations in the form of capsules or liquid preparations, and thus can be used in dental applications. Also, the aqueous solution of the present invention can be used in either tooth remineralization-promoting agents for promoting remineralization of tooth enamel or anti-hypersensitivity agents for treating hypersensitive teeth caused by exposure of dentinal tubules. Furthermore, the aqueous solution of the present invention can also be used for the same purposes in mouth care products such as tooth paste or mouth washes.

Although the preferred embodiment of the present invention has been described for illustrative purposes, those skilled in the art will appreciate that various modifications, additions and substitutions are possible, without departing from the scope and spirit of the invention as disclosed in the accompanying claims.

The invention claimed is:

1. A method for preparing an aqueous solution of high-concentration calcium phosphate, the method comprising the steps of:
    preparing an acidic aqueous solution using an acidic chelating agent;
    dissolving a calcium phosphate-based compound in the acidic aqueous solution to obtain an aqueous calcium phosphate solution; and
    adding a pH-adjusting agent to the aqueous calcium phosphate solution increase the pH of the aqueous solution.

2. The method of claim 1, wherein phosphoric acid ($H_3PO_4$) is further added to the aqueous calcium phosphate solution.

3. The method of claim 1, wherein the acidic chelating agent is any one selected from citric acid and EDTA (ethylene diamine tetra-acetic acid).

4. The method of claim 1, wherein the calcium phosphate-based compound is at least one selected from the group of hydroxyapatite, carbonated apatite $Ca_{10}$, tricalcium phosphate, and calcium hydrogen phosphate.

5. The method of claim 1, wherein the pH-adjusting agent is at least one selected from sodium hydroxide and sodium hydrogen carbonate.

6. The method of claim 1, wherein the acidic aqueous solution and the calcium phosphate-based compound are an aqueous citric acid solution and nano-sized carbonated apatite (n-CAP), respectively.

7. The method of claim 6, wherein the citric acid and the n-CAP are used at concentrations of 0.3 wt % or less and 0.25 wt % or less, respectively, based on the total weight of the aqueous calcium phosphate solution.

8. The method of claim 6, wherein the citric acid and the n-CAP are used at concentrations of 0.1 wt %, respectively, based on the total weight of the aqueous calcium phosphate solution.

9. The method of claim 1, wherein the pH of the aqueous calcium phosphate solution is in the range from 5.5 to 6.1.

10. The method of claim 2, wherein the phosphoric acid is added in an amount of 0.0012~0.006 wt % based on the total weight of the aqueous calcium phosphate solution.

11. The method of claim 10, wherein the phosphoric acid is added in an amount of 0.0024 wt % based on the total weight of the aqueous calcium phosphate solution.

* * * * *